US007247858B2

(12) United States Patent
De Keyser (10) Patent No.: US 7,247,858 B2
(45) Date of Patent: Jul. 24, 2007

(54) METHOD FOR CREATING A CONTIGUOUS IMAGE USING MULTIPLE X-RAY IMAGERS

(75) Inventor: Paul De Keyser, Puurs (BE)

(73) Assignee: Agfa HealthCare, N.V., Mortsel (BE)

( * ) Notice: Subject to any disclaimer, the term of this patent is extended or adjusted under 35 U.S.C. 154(b) by 276 days.

(21) Appl. No.: 10/818,531

(22) Filed: Apr. 5, 2004

(65) Prior Publication Data

US 2004/0200971 A1   Oct. 14, 2004

Related U.S. Application Data

(60) Provisional application No. 60/464,967, filed on Apr. 23, 2003.

(30) Foreign Application Priority Data

Apr. 10, 2003  (EP) ................... 03100959

(51) Int. Cl.
G01T 1/24 (2006.01)
H01L 25/00 (2006.01)
H01L 27/00 (2006.01)
(52) U.S. Cl. .................. 250/370.09; 250/370.01; 250/370.08
(58) Field of Classification Search .......... 250/370.09, 250/370.01, 370.08
See application file for complete search history.

(56) References Cited

U.S. PATENT DOCUMENTS 4,467,342 A * 8/1984 Tower ................ 257/443
4,503,460 A    3/1985 Sklebitz
5,572,037 A * 11/1996 Liu et al. ............ 250/483.1
6,038,286 A    3/2000 Wagli et al.
6,069,361 A * 5/2000 Rubinstein ............ 250/370.11
6,207,944 B1 * 3/2001 Spartiotis et al. ........ 250/208.1
6,323,475 B1   11/2001 Spartiotis et al.
6,403,964 B1 * 6/2002 Kyyhkynen ............ 250/370.09

FOREIGN PATENT DOCUMENTS

| DE | 200 00 603 U 1 | 5/2000 |
| EP | 0 262 267 A1 | 4/1988 |
| EP | 0 421 869 A1 | 4/1991 |
| EP | 0 618 719 A1 | 10/1994 |
| EP | 0 919 858 A1 | 6/1999 |
| EP | 1 162 833 A1 | 12/2001 |
| EP | 03 10 0959 | 8/2003 |
| JP | 03137589 A * | 6/1991 |
| WO | WO 91/10921 | 7/1991 |
| WO | WO 99/33117 | 7/1999 |

* cited by examiner

Primary Examiner—David Porta
Assistant Examiner—David S. Baker
(74) Attorney, Agent, or Firm—Houston Eliseeva LLP (57) ABSTRACT

A radiographic image is obtained by combining at least two radiographic sub-images acquired by at least an upper and lower 2-dimensional radiation sensor having sensor pixels. The radiation sensitive area of the lower sensor is overlapped by the upper sensor. Overlap is preferably at least two pixel rows, but can also be limited to non-imaging parts of the upper sensor. The radiation sensors may comprise a radiation to light converting layer.

Preferably the sensors are built using CMOS technology, exhibiting less radiation absorption outside the radiation sensitive area.

16 Claims, 4 Drawing Sheets

METHOD FOR CREATING A CONTIGUOUS IMAGE USING MULTIPLE X-RAY IMAGERS

The application claims the benefit of U.S. Provisional Application No. 60/464,967 filed Apr. 23, 2003.

FIELD OF THE INVENTION

The present invention relates to a method for obtaining an image using direct digital radiographic imaging.

More specifically the invention is related to direct digital radiography using multiple sensors.

BACKGROUND OF THE INVENTION

Traditionally, analog radiographic imaging, e.g. in medical applications, is performed using a combination of a phosphor layer, converting the X-rays to light, and a photographic film, e.g. 35*43 cm for a relatively large field of view as used in chest x-rays. The light emitted by the phosphor is captured by the film which is developed to obtain an image on the film.

Direct methods using only a film without a phosphor layer exist but are characterised by a low efficiency and can not be used for medical applications due to the need of high radiation dose needed to expose the film.

Both methods have the drawback that the photographic film has to be chemically processed, leading to chemical waste products and loss of time.

The first digital X-ray systems, now known as computed radiography (CR), used a stored energy releasing phosphor sheet which is exposed to a radiation image during X-ray exposure. The stimulable phosphor stores the radiation image at exposure whereafter the stored energy image is read out using stimulating radiation scanning the phosphor plate, releasing the image-wise stored energy as light. The light is detected and an electronic image is generated by the light detector and processing electronics, whereafter it is digitised. There is always a loss of time between the X-ray exposure and the readout of the image. Changing of the phosphor plates for the subsequent exposures is also cumbersome and requires intervention by the operator of the imaging apparatus.

Direct digital X-ray systems (DR) reading out the radiation image in real time using electronic sensors do exist. The systems can be divided in two main classes:

1. Systems using direct X ray conversion to electrons. The incident radiation reaches a photoconductor material which transforms the radiation into electron-hole pairs in response to the intensity of e.g. the X-rays. Charges generated are collected in a silicon based chip supporting the photoconductor. Conversion materials typically used are amorphous Selenium, Mo, lead iodide, mercury iodide, CdTe CdZnTe etc.
2. Presently most systems use indirect conversion sensors having a scintillator or phosphor layer as conversion layer converting the X-ray into visible light which is then detected with an electronic light sensor array which converts the light into electrons. Used materials in the conversion layer may be e.g. Gadolinium oxysulfide or cesium iodide.

It is essential that the conversion layer absorbs a significant part of the X-rays to achieve efficient detection, and thus the lowest possible dose to the patient. Well-designed electronic system should typically reach double efficiency versus film-based X-ray detection.

Detailed discussion of existing digital systems and drawbacks:

The majority of the current systems are flat panels made with amorphous Silicon technology. These are matrix arrays of a-Si addressing transistors covered with a photoconductor material in case of type 1. In case 2, these are matrix arrays of a-Si addressing transistors and a-Si photodiodes, covered with a phosphor. Size up to 43×43 cm is not a problem with these panels.

A first disadvantage however is that pixel resolution is currently limited, as amorphous silicon, due to its physical properties, does hardly allow to fabricate pixels smaller than some 100 microns square.

A second disadvantage lies in the fact that currently these panels are of the passive type, i.e. have no in-pixel amplification capability. This makes fast imaging (i.e. continuously producing more than 1 image per second) very cumbersome and expensive.

In principle, a detector using crystalline Si or another high-quality semiconductor material would be far superior in terms of smaller pixel size reachable, and due to the possibility of in-pixel circuitry such as amplifiers which greatly helps for higher imaging speeds. The major problem is that the (silicon) wafers used to make such detectors are limited in size. Large wafers are very costly and also the yield of the production process can be low. I.e. the percentage of good sensors out of a production run decreases very rapidly with increasing size.

An existing solution, indeed making use of crystalline detectors such as CCDs or CMOS sensors for indirect detection, to this problem is that the light image generated by the conversion layer is reduced and imaged to the small image sensor by an optical system. This may be a lens system or an optical fibre system.

The most important drawbacks of this method are:

Due to the reduction of the image a relatively low number of pixels are read out for a large image, resulting in an inferior image quality, due to lower resolution.

A significant portion of the light is lost, leading to lower detection efficiency and/or higher dose to the patient. This happens because with the current state of the technology, and with demagnifications higher than five to ten times, unless expensive cooling mechanisms are used, the electronic noise from the detector system will be so high in comparison with the electronic signal, that the intrinsic signal-to-noise ratio of the X-ray signal is significantly degraded.

The bulky optics does not allow that the readout system is housed inside e.g. a conventional X-ray cassette. This would be desirable however, as a system which can be housed in a cassette with the form factor of a conventional X-ray cassette could then be plugged into a conventional X-ray apparatus. This would allow an easy upgrade from analog to digital imaging workflow, whereby the existing X-ray apparatus does not have to be replaced entirely.

Standard cassettes are provided in several sizes for different applications and dimensions and specifications of cassettes are regulated by international approved standards such as ANSI Ph 1.49.

In order to avoid undesirable low number of pixels mentioned above, systems have been sought to split up the large field of view into smaller sections, each covered by a separate imager. The method for doing this should however:

not show any visible greyscale response or differences between individual image sensors. This can usually be solved with proper calibration techniques.

Not lose any image information in between the image sensors. This is not so easy to do, and several approaches exist to try to circumvent this problem. These will now be described.

Several prior art systems exist to make one large image using multiple image sensors:

Techniques try to minimise or even eliminate the spacing between the border pixels of the individual imagers by bringing them close together (butting).

Linear butting of sensors can be found in several documents:

In EP 262 267 an image-receiving plane is made up of a two-dimensional array of radiation detectors, each having his own image processing circuit. In between the sensors however insensitive gaps exist.

U.S. Pat. No. 6,207,944 describes a sensor in which the edge pixels are larger in order to provide butting of the different sensors. However by providing a larger edge pixel generates a distortion to the image at the location of the butting lines.

Likewise in U.S. Pat. No. 6,323,475 conductive tracks lead from the selected detector positions to offset readout circuit positions allowing for certain pixels to be bigger than others.

In WO 99/33 117 several imaging device tiles are very accurately mounted on a support structure.

Especially the very accurate mounting poses problems in fabrication and makes such a combination of imaging tiles costly. It is requires high-precision machining technology to cut the silicon very precisely. And high precision machinery is needed to mount the chips together. This is costly and complex.

In EPA-1 162 833 sensors are mounted to butt sensitive areas. In one direction the chips overlie each other while in the other direction the chips are butted. The problem is that typically the edges of chips can not be brought close together than 50-100 microns, leaving a gap in between that is not light-sensitive and thus could miss vital (in other words: possibly lethal, e.g. a small cancer trace) information.

Also other systems make use of overlap of sensors in one directions in order to bring pixels closer together and not to loose information. Such system can also be found in EP 421 869. A very accurate overlapping of the chips provides butting of the sensitive areas.

In U.S. Pat. No. 4,467,342 CCD chips for detecting radiant energy have an overlap joint without substantial phase difference occurring at the lap joint. The major difficulty is to align the sensors accurately. CCD sensors exhibit low efficiency for radiation image sensing.

Another approach is using multiple cameras providing overlapping images of a e.g. scintillator screen.

In U.S. Pat. No. 4,503,460, DE 20000603 and EP 618 719 a combination of plural television pickup devices coupled to one X-ray intensifier using optics is used. Various detected regions overlap. The system has the drawback that due to the use of lenses the apparatus is large and can not be retrofitted in existing machines and x-ray cassettes. These systems have the advantage that no information is missing in between the separate images. They have however also a lower light efficiency, the cost of the multiple systems and due to their thickness usually do not fit in a conventional film-based X ray system.

U.S. Pat. No. 6,038,286 makes use of mirrors to divide the image towards several camera systems. This system has nearly the same drawbacks as it uses multiple cameras. The height is however somewhat less. Overlap seam problems may however occur at the mirror's edges.

WO 91/10921 describes the use of the transparency of silicon when using DRAM Chips having large spaces between cells as imaging sensors. Large spaces in between cells is however not acceptable for medical applications.

Other systems use mechanical step and repeat systems successively positioning the sensors at different positions. Mechanical systems are however slow, expensive and pose on the long term reliability problems. These systems can e.g. not be used for in vivo diagnostics.

In conclusion, the current state of the art is that imagers are either butted and in such case there is always a compromise on the image detail at the seams, and positioning is cumbersome and expensive; or a camera-like approach is used, but in such case the detector assembly rapidly becomes too thick to allow insertion into conventional analog X-ray units.

There is thus a need for a digital x-ray detection system possible combining several desired properties:

having a relatively large sensing area with sufficient pixel density.

having low enough noise to produce more than one image per second, being flat enough to allow insertion in conventional X-ray units, not missing or significantly compromising parts of the image due to imperfect butting of the different imagers the detector plane is composed off, and allowing at the same time low-cost manufacturing techniques for positioning the different imagers.

SUMMARY OF THE INVENTION

The desirable features and avoidance of the above-mentioned drawbacks can be realised by a method having the specific features set out in claim 1.

Specific features for preferred embodiments of the invention are set out in the dependent claims.

Further advantages and embodiments of the present invention will become apparent from the following description and drawings.

DETAILED DESCRIPTION OF THE INVENTION

While the present invention will hereinafter be described in connection with preferred embodiments thereof, it will be understood that it is not intended to limit the invention to those embodiments.

The drawbacks of the state of the art imaging methods are avoided by a method according to the present invention.

Principle

Use is made of the fact that for most x-ray diagnostic energies, the used semiconductor materials used in electronics, such as crystalline and amorphous Si and Ge, GaAs, Se, CdSe . . . , are due to their low atomic weight partially transparent to the radiation at wafer thickness used in electronics. On top of that, they will also hardly scatter this radiation and thus avoid blurring.

As an illustration regarding the transparency of the silicon sensors, e.g. at 20 KeV, which is used in mammography, a 350 micron wafer attenuates the beam by approximately 50%. Still half of the radiation energy is available behind the wafer.

Also, below 100 KeV, interaction of the Silicon with the radiation is mainly through absorption via the photo-electric effect, and there is almost no scattering present which could lead to inferior image quality such as blurring.

Even better characteristics can be obtained by thinning the wafers by an extra processing step applied to the back of the wafers. This provides better transmission of the X-ray to the underlying wafers which is especially desirable for lower energies.

This makes it possible to position the different imaging sensors in an overlapping configuration with only minor signal-to-noise compromise in the overlap region, and making it possible to acquire a contiguous image of large area starting from several sub-images. If e.g. 40% of the radiation would be lost in the silicon before being converted in the scintillator, it can be calculated from physics that the SNR degradation would be only 25% or less than 3 dB.

The parts of the sensor, which do not make use of the incident radiation, are as low absorbent as possible to let the radiation pass through to the next underlying sensor where needed, while radiation conversion layers (either scintillator or photoconductor type) try to achieve high efficiency by absorbing and converting as much of the radiation as possible into light or electrons for the top sensor.

The advantage of using e.g. CMOS technology as basis for the sensor chips is that this technology is a mature technology well known and very controllable in the production process. Each pixel can typically be structured so as to be "active", i.e. having an amplification circuit on its own.

The sensors can be made with a minimum of insensitive inter-pixel area.

Also, in contrast with CCDs, CMOS sensors can be devised such that they are radiation-hard, i.e. their performance will not or only slightly degrade due to exposure with X-ray photons.

Alternatively other types of sensors such as CCD's, amorphous silicon sensors, . . . can still be used.

The method according to the invention is characterised in that the two dimensional silicon sensors are made to overlap each other relative to the direction of the incident radiation of the exposure.

The method according to the invention obtains a radiographic image by acquiring at least two radiographic sub-images using at least an upper and a lower 2-dimensional radiation sensor, overlapping relative to the direction of the radiation source.

A single radiographic exposure from a radiation source is used for obtaining the sub-images. Each of the sensors has a radiation sensitive area comprising pixels. The radiation sensitive area of the lower sensor is overlapped by the upper sensor.

After acquiring the sub-images they are combined to obtain the combined radiographic image.

Overlap Configuration

It is possible to let the light sensitive area of the lower sensor overlap by the upper sensor without being overlapped by the radiation sensitive area of the upper sensor.

It is possible to exactly align the pixel grids of the sensors to obtain a combined image. This in itself would allow, by careful positioning, to fabricate imagers where the respective areas would be perfectly butted, i.e. versus the (point-like) X-ray source, the conversion layer edges projections would exactly touch each other, or at least within a tolerance smaller than e.g. a quarter of the pixel size. The acquired sub-images would exactly align along each other.

The physical overlap along the direction of the sensors themselves would need to vary dependent upon the angle at which the penetrating radiation reaches the sensors seams.

Although this is a possible embodiment of this invention, it would require relatively costly equipment for positioning the components with these tight tolerances.

A preferred embodiment of the present invention therefore uses sensors with overlap of the radiation sensitive areas, as projected downward on each other, away from the point-like X-ray source. The radiation sensitive area is considered to be the area comprising sensor pixels covered by the conversion layer and where image detection is performed. This means that in this area both the radiation conversion and detection of the converted radiation by the sensor takes place.

Using this method it is possible to construct a contiguous image from the sensors overlapping sub-images which truly represents the X-ray image without the physical alignment problem.

And a total image is obtained which is guaranteed not to miss any geometrical details where the detectors meet.

Preferably the overlap between the radiation sensitive areas of the sensors is at least two rows but a larger number of overlap pixel rows can be provided.

The construction of the combined image is done in a processing section.

Figure 1:
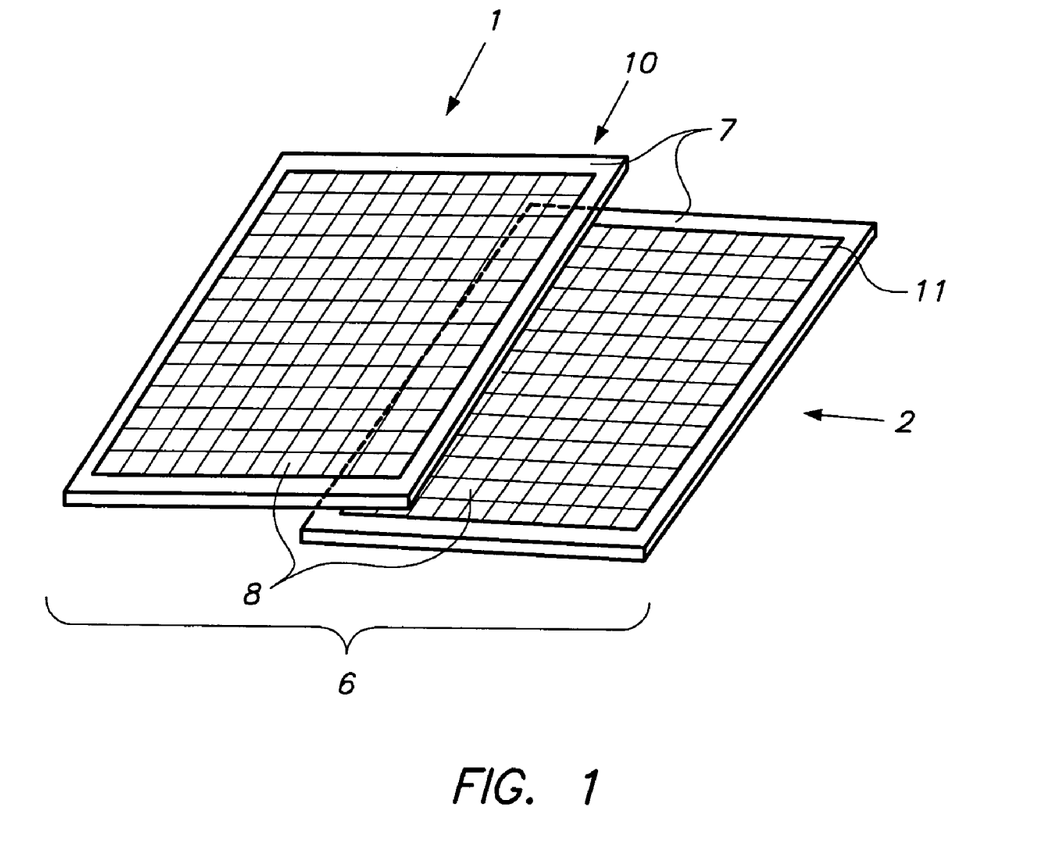
FIG. 1 illustrates the mounting of two overlapping image sensors
Figure 2A:
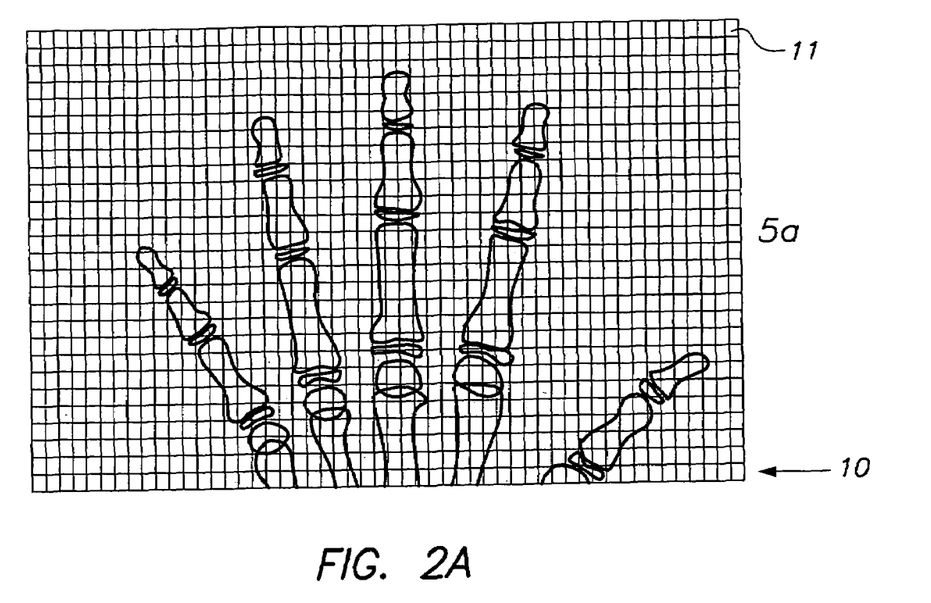
FIGS. 2A and 2B show the images acquired by the two overlapping sensor wafers during the exposure.
Figure 2B:
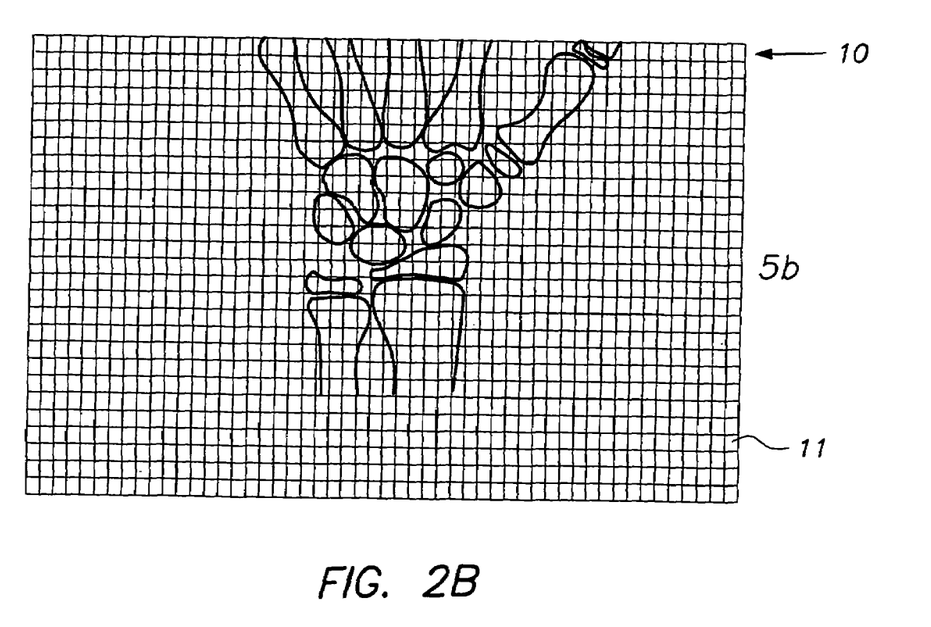

FIG. 1 depicts two overlapping image sensors 1,2 as can be used in an imaging assembly 3, sensed images 5*a*, 5*b* are shown in FIGS. 2A and 2B. The sensors 1,2 are built on a CMOS chip comprising a non-sensitive edge 7 and a central radiation sensitive pixel grid 8 overlaid by a conversion layer 9. The conversion layer 9 can be of the direct or indirect type. As mentioned above the sensors chips 1,2 have an overlap of at least one pixel row 10 but preferably an overlap of 2 pixel rows 10 is provided.

Single Exposure

The sensors 1,2 both acquire a sub-image 5*a*, 5*b* during a single radiographic exposure. This means they acquire a sub-image 5*a*, 5*b* at the same time.

A single exposure may be a continuous intensity exposure during a certain exposure time or the radiation source (e.g. X-ray tube) can be used in another mode, e.g. exposure methods are known wherein the radiation source is varied in intensity or the x-ray tube is driven in a pulsed manner. These modes are usually combined with a sensor to detect the radiation dose already received and to regulate in real-time the exposure in view the density of the object to be examined.

Sub-Image Combining

When combining the sub-images 5*a*, 5*b* of overlapping sensors chips 1, 2 in a processing assembly certain issues have to be addressed.

Due to variability in the fabrication of the sensor wafers 1, 2 and the application of the conversion layers 9, it is possible that not all pixel elements 11 have the same conversion efficiency.

Calibration algorithms will also have to be used in order to correct for intensity differences in received radiation itself and in differences in gain and offset of the sensor pixels 11. This allows for correction of differences in conversion efficiency between sensors 1, 2 as well as between sensor pixels 11 from the same sensor wafer.

After automatic calibration of the sub-images 5a, 5b the proper image information for each location in the image can be retrieved. The ultimate goal is to obtain an image wherein the signal levels or optical densities of the examined object corresponds to the physical density of the object of the radiation used.

Another problem is a problem regarding location of the imagers 1, 2. The sub-images 5a, 5b acquired by the two overlapping sensor wafers 1, 2 in FIG. 1 during the exposure are shown in FIGS. 2A and 2B.

It can be seen that the pixel grid 8 of the sensors 1, 2 always slightly differs from the ideal position and angle. This poses problems in constructing a composite image 5 for the whole examination area.

To avoid expensive an tedious alignment of the sensors 1, 2 the sub-images 5a, 5b are combined electronically and/or via software. In EP 866 342 and EP 919 858 two or more images obtained by readout of stimulable phosphor plates are likewise combined. Also here calibration of the algorithm is needed.

This can be done by imaging a grid or pattern and retrieving the precise (relative) location of each sensor chip relative to the other. By interpolation algorithms and other image processing techniques, such as a two dimensional warping transformation, the sub-images 2a, 2b can be combined to one image.

As the sensors 1, 2 are mounted together in a fixed position to each other, the calibration of the algorithm has to be executed only once.

Preferably the calibration grid, which may be included in a x-ray phantom, uses a grid comprising slanted lines. This allows for detection of shift and rotation of one pixel grid 8 to another.

Figure 3:
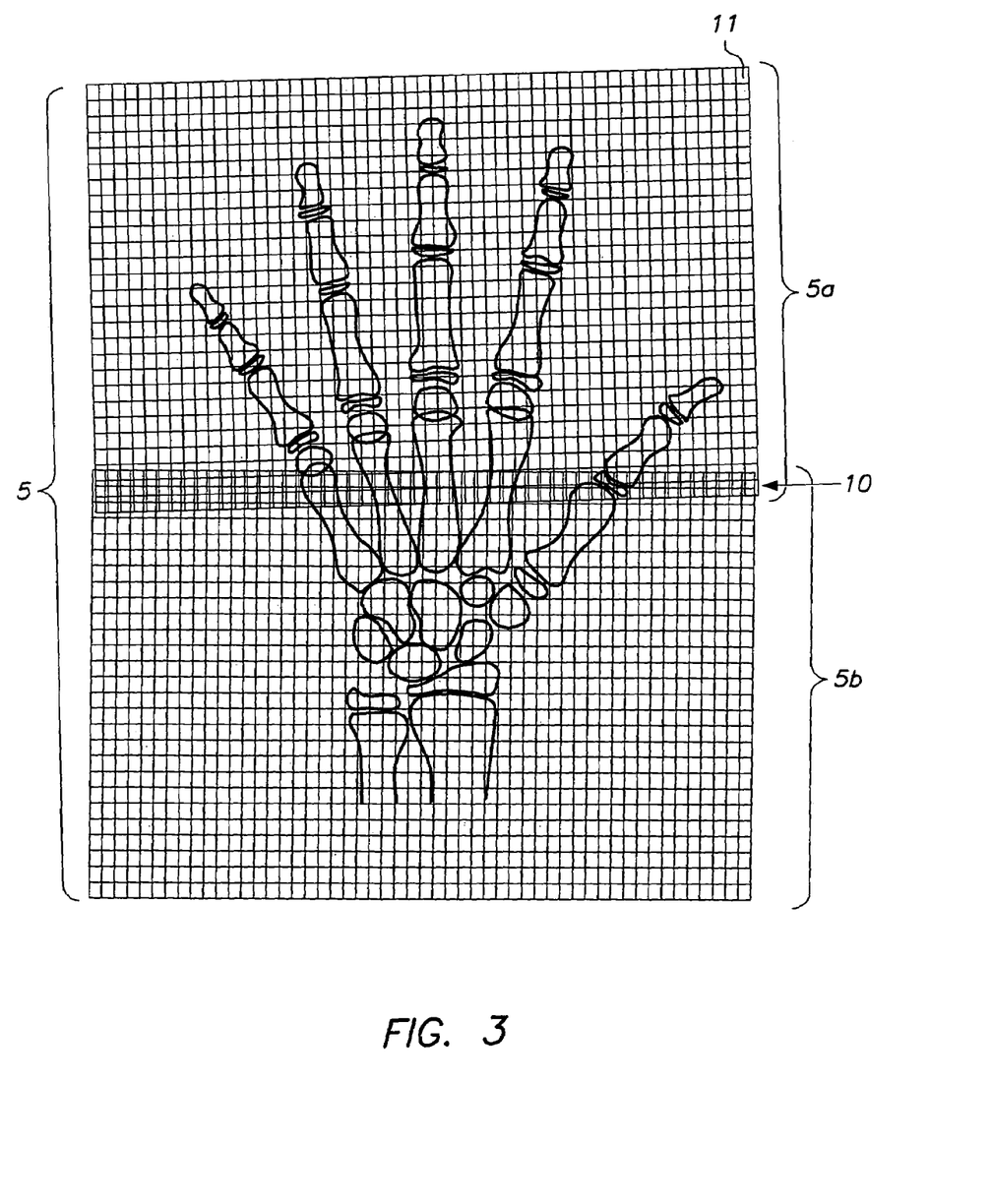
FIG. 3 shows the resulting image from the combination of the two sub-images.

An example of the resulting image of combinations of the two sub-images 5a, 5b is shown in FIG. 3.

As mentioned the combining of the sub-images 5a, 5b is done in a processing section which is besides the radiation sensors 1, 2 also a part of the imaging assembly 6. The processing section for performing the calibrations and merging of the images 5a, 5b is normally located very close to the sensors 1, 2 but it is possible to locate the processing section at a greater distance when necessary, e.g. due to space considerations.

The advantages of a method according to the present inventions are numerous:

A larger area can be imaged using high resolution combined imagers 1, 2, . . . without inter pixel radiation insensitive areas. However, it will be clear that in case of more than 2×2 detectors, also connecting wires etc. will have to be attached such that they do not or only minimally interfere with the image.

Easier and cheaper mounting of the sensors 1, 2, . . . due to allowable overlap of the sensors 1, 2, . . .

By using overlapping sensors 1, 2, . . . without optics the sensor assembly 6 can be housed in the equivalence of a state of the art X-ray cassette, giving the possibility to retrofit an existing X-ray apparatus with a module for acquiring direct X-ray images. It is also possible to retrofit a radiographic apparatus which uses stored energy releasing phosphor cassettes. At least the sensors 1, 2, . . . of the radiographic imaging assembly 6 are mounted inside the radiographic film cassette. Preferably also the processing section is located inside the cassette.

Figure 4:
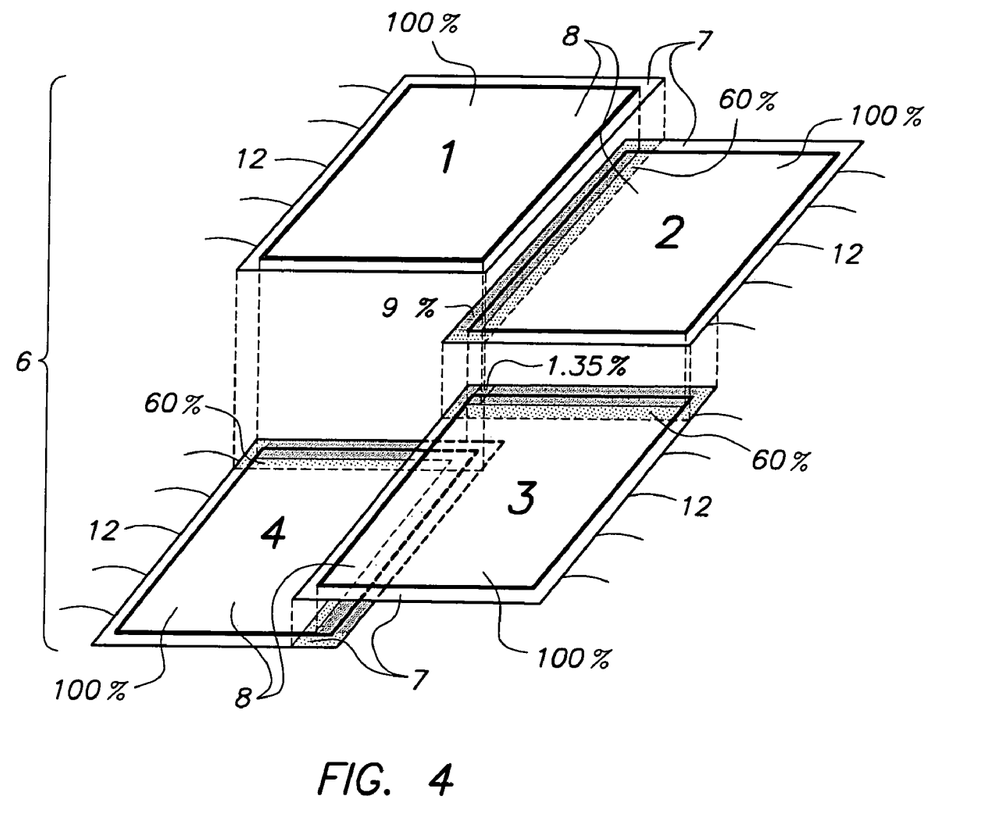
FIG. 4 shows a view of 4 overlapping sensors.

FIG. 4 gives an example of an assembly 6 of 4 overlapping sensors 1, 2, 3 and 4.

Each sensor wafer 1-4 has a dimension of about 10 cm×10 cm so the combined area has a size of about 20 cm×20 cm.

The wafers 1-4 are fabricated using crystalline Silicon using CMOS technology. Normally they have a thickness of about 750 μm. The chips 1-4 can however be thinned by the above mentioned techniques. The thickness of the wafer 1-4 can be reduced to dimensions of 350 μm.

The radiation used in this example has an energy of about 18 KeV although energy levels up to 100 KeV can be used. The thickness of the wafer 1 in combination with the energy of the penetrating radiation results in a approximately 50% transmission of the radiation through the wafer where it is not covered by the conversion layer 9.

The conversion layer 9 overlying the photosensitive pixel grids 8 of the wafer 1-8 is a layer of Gadolinium oxysulfide phosphor having a thickness of about 50 μm. This layer has an absorption coefficient of 80% for the used radiation and thus provides a high conversion efficiency.

Preferably the sensors 1-4 are of the CMOS APS (active pixel sensor) type. These sensors utilise active transistors in each pixel 11 to buffer the photo-signal. Following characteristics can be achieved:

X-Y addressability—small, pixel size (10 μm)

Low noise (<30 e r.m.s., single read), if need be with cooling

High dynamic range (80 dB)

Good quantum efficiency (approximately 25% peak photogate mode, 50% peak photodiode mode).

Large formats (up to 1K×1K demonstrated).

Single +5 volt (or +3 volt) power supply operation.

High Speed Electronic shutter (<100 usec. exposure)

Great Antiblooming (more than 100×saturation)

No image lag, >80 db suppression

On-chip timing, control, signal chain electronics

Low Power

Radiation resistant compared to CCDs if special measures are taken.

The voltages are readout from the chip 1-4 using the active transistors and the signals are digitised to obtain digital sub-images acquired by the separate sensors. Alternatively the sensors chips 1-4 include digitising means for direct outputting a digital image signal to the image processing means. Leads 13 to readout the sub-images from the sensors are provided at edge of the sensors 1-4 at the outside of the combined imaging region.

In the image processing sections the sub-images are combined using interpolation algorithms and other image processing techniques, such as a two dimensional warping transformation.

Possible applications of the 4 sensor assembly 6 can e.g. be found in Mammographic imaging, mobile radiology imaging, non-destructive material testing and in radiographic imaging of small mammals in veterinary radiology.

Further Possible Embodiments

Figure 5:
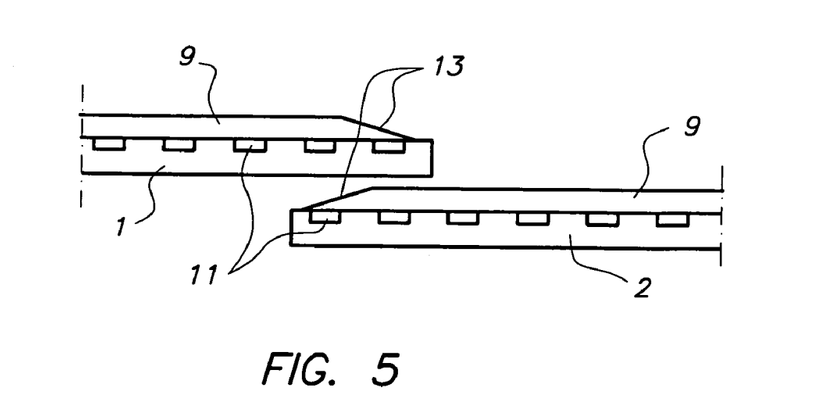
FIG. 5 shows two overlapping sensors having a conversion layer with bevelled edges.

The edge of the phosphor conversion layer 6 of the top wafer gives a sharp shadow in the image acquired by the underlying sensors 2-4. In another possible embodiment shown in FIG. 5 the overlapping phosphor layers 9 can both be constructed having bevelled edges 14. This provides a smooth transition of the image of a overlying sensor 1 to the image of the underlying sensor 2. Calculations of the image information in the common area 8 can be based on the measurements of both sensors 1, 2 giving an image without any visual lines.

It can be understood that above clarification and embodiments are not restricted to X-ray apparatus. Any kind of penetrating radiation can be used, depending upon the application field and the object to be imaged.

The term X-ray sensor is therefore not limited to a sensor for so called X-ray radiation, but is to be understood as a sensor which can be used for detecting any kind of penetrating electromagnetic radiation in its broadest sense.

Signal to Noise Considerations

Like all imaging systems the sensors exhibit a certain signal to noise ratio. The system is also a so-called photon shot noise limited system. Each overlying sensor chip has a certain absorption and weakens the incoming signal of the underlying sensors 2-4. For area of the bottom sensor 4 which is overlapped by 3 sensors the incoming signal is weakened and the signal-to-noise ratio decreases. Let A be the adsorption percentage of the non imaging area of a single CMOS sensor chip . Then in the so-called Poisson-limited case, this means that for the fourth sensor 4 the SNR will be reduced by a factor sqrt[(1-Absorption)**3] for the areas where the penetrating radiation is unattenuated by an object.

Further noise can be added due to noise from the electronic circuits, e.g. thermal noise, before digitalisation is done.

A possible and preferable improvement of the method can be obtained by cooling the sensor chips 1-4. Thermal noise is thus reduced and its influence can be neglected. This also allows for the use of a lower radiation intensity during X-ray exposure which is important in the medical field, reducing the radiation dose administered to the patient. More specifically this will be useful in dynamic imaging procedures, where video-like sequences of images are obtained, e.g. to guide surgery. In such case, more than 1 and up to 30 images per second might be captured.

Cooling of the elements can be done using a Peltier-element or by other means available.

Normally by lowering the temperature about 8 degrees Celsius, noise can be reduced by 50%.

Most 2-dimensional radiation sensors 1-4 are of the indirect type comprising a conversion layer 9 converting the radiation into light.

A variant of the method use sensors having a direct conversion layer 9 converting the electromagnetic radiation directly to electrons.

Such layers can be made of photoconductive materials.

When the photoconductor is closely coupled to the sensing pixel a high conversion efficiency can be obtained.

However the choice of an ideal composition of the x-ray to electrons or photoconductor layer in relation to the used radiation is very important to obtain high sensitivity.

A possible direct conversion layer 9 is amorphous Selenium having a thickness of up to 500 µm. To operate this sensors it is necessary to charge this layer. The photoconductor layer may for certain applications be charged with a voltage up to 5000V.

Also direct radiation sensors do exist which do not make use of conversion layers 9, but use the silicon itself instead. These sensors however require a high radiation dose and are limited to applications in the field of non destructive testing.

Having described in detail preferred embodiments of the current invention, it will now be apparent to those skilled in the art that numerous modifications can be made therein without departing from the scope of the invention as defined in the appending claims.

PARTS LIST

1-4. image sensor, sensor chip
5. composite image
5*a*. first sub-image
5*b*. second sub-image
6. imaging assembly
7. non-radiation sensitive edge
8. radiation sensitive grid
9. conversion layer
10. overlapping pixel rows
11. individual pixel
12. readout leads
13. bevelled edges of conversion layer.

The invention claimed is:

1. Method for obtaining a radiographic image comprising the steps of:
   acquiring a number of radiographic sub-images during a single radiographic exposure from a radiation source, using upper and lower 2-dimensional radiation sensors relative to the direction of the radiation source, the sensors each having a radiation sensitive area comprising pixels and a conversion layer that converts radiation from the radiation source for detection by the pixels, the conversion layer being positioned between corresponding one of the sensors and the radiation source,
   combining the acquired radiographic sub-images to obtain a combined radiographic image,
   wherein the two 2-dimensional radiation sensors partially overlap each other in two dimensions with a radiation sensitive part of the lower sensor being partially overlapped by the upper radiation sensor in a direction moving away from the radiation source.

2. The method according to claim 1 wherein the pixels are arranged in rows and wherein the overlap of the radiation sensitive areas is at least two rows of the pixels.

3. The method according to claim 2 wherein the 2-dimensional radiation sensors are indirect radiation sensors with the conversion layers converting the radiation to light.

4. The method according to claim 2 wherein the conversion layers are direct conversion layers or photoconductor layers, which convert the radiation into electrons directly.

5. The method according to claim 1 wherein the 2-dimensional radiation sensors are indirect radiation sensors with the conversion layers converting the radiation to light.

6. The method according to claim 1 wherein the conversion layers are direct conversion layers or photoconductor layers, which convert the radiation into electrons directly.

7. Method according to claim 1 wherein the conversion layers are beveled toward the edges in the overlapping region.

8. The method according to claim 1 wherein the radiation sensors are based on CMOS technology.

9. The method according to claim 1 wherein the radiation sensors are cooled.

10. Radiographic imaging assembly comprising:
    upper and lower 2-dimensional radiation sensors, for acquiring a number of radiographic sub-images during a single radiographic exposure, said sensors having partially overlapping radiation sensitive areas in two dimensions in a direction of incident radiation, each of the radiation sensors having a conversion layer for enabling detection of the incident radiation by the radiation sensitive areas, the conversion layer of each of the radiation sensors being located between the corresponding one of the sensors and a source of the incident radiation, a combiner for combining the acquired images to obtain a single combined radiographic image.

11. The assembly according to claim 10, wherein the conversion layer of each of the radiation sensors converts x-ray radiation into light on each one of the upper and lower radiation sensors.

12. The assembly according to claim 11 wherein the conversion layer of each of the radiation sensors is beveled toward edges in an overlapping region.

13. Radiographic imaging assembly according to claim 10 wherein the radiation sensors are mounted into a radiographic cassette for mounting into a radiographic apparatus capable of using standard radiographic film or phosphor cassettes.

14. The assembly according to claim 10 wherein pixels of the upper and lower radiation sensors are arranged in rows and wherein the overlap is at least two rows of the pixels.

15. Radiographic imaging system comprising:

an radiation source generating x-ray radiation;

four radiation sensors for acquiring respective radiographic sub-images, each of the four radiation sensors comprising a radiation sensitive area comprising a two-dimensional grid of pixels and a conversion layer facing the radiation source, wherein the two-dimensional grid of pixels of each one of the four radiation sensors partially overlaps the two-dimensional grid of pixels of at least one other two-dimensional grid of pixels in a direction of the x-ray radiation; and a processing section for combining the acquired sub-images to obtain a single combined radiographic image from the same radiographic exposure.

16. A system as claimed in claim 15, wherein the two-dimensional grid of pixels of each one of the four radiation sensors partially overlaps the two-dimensional grid of pixels of at least two other two-dimensional grid of pixels in a direction of the x-ray radiation.

* * * * *